United States Patent
Masarczyk et al.

(10) Patent No.: US 6,591,659 B1
(45) Date of Patent: Jul. 15, 2003

(54) PROCESS FOR THE DETERMINATION OF THE FRICTION PROPERTIES OF SHEET METAL DURING FORMING AND THE MEASURING APPARATUS FOR CARRYING OUT THE PROCESS

(75) Inventors: Peter Paul Masarczyk, Bochum (DE); Thomas Struppek, Werne (DE)

(73) Assignee: Thyssen Krupp Stahl AG, Dusseldorf (DE)

( * ) Notice: Subject to any disclaimer, the term of this patent is extended or adjusted under 35 U.S.C. 154(b) by 233 days.

(21) Appl. No.: 09/678,815

(22) Filed: Oct. 4, 2000

(30) Foreign Application Priority Data

Oct. 6, 1999 (DE) .......................... 199 47 955

(51) Int. Cl.⁷ .............................. G01N 19/02
(52) U.S. Cl. .................................. 73/9
(58) Field of Search ........................ 73/9, 10

(56) References Cited

U.S. PATENT DOCUMENTS

| | | |
|---|---|---|
| 3,033,019 A | 5/1962 | Oliver |
| 5,490,410 A | 2/1996 | Markström |
| 5,996,395 A * | 12/1999 | Nagasawa et al. ............ 73/9 |

FOREIGN PATENT DOCUMENTS

| | | |
|---|---|---|
| EP | 0 491 234 A | 6/1992 |
| EP | 0 874 230 A | 10/1998 |
| FR | 2 531 778 A | 2/1984 |
| FR | 2 660 756 A | 10/1991 |
| GB | 1494274 | * 12/1977 ............ 73/9 |

OTHER PUBLICATIONS

Kitchen et al., "Realistic Friction Testing", Corning Corp, Mar. 1967.*

* cited by examiner

Primary Examiner—Robert Raevis
(74) Attorney, Agent, or Firm—Proskauer Rose LLP

(57) ABSTRACT

The invention relates to a process and a measuring apparatus for determining the friction characteristics of sheet metal during forming. To do this, a strip-shaped sample of sheet metal (1) is clamped between two gripping jaws (2, 3) and drawn by a drawing device (9), for preference at a constant drawing speed. During the drawing, the surface pressure ($F_N$) is continually increased. From the values allocated to the surface pressure ($F_N$) and to the drawing force ($F_Z$), applying the known formula $\mu = F_R/F_N$, the friction characteristics dependent on the surface pressure are calculated.

12 Claims, 3 Drawing Sheets

Figure 1:
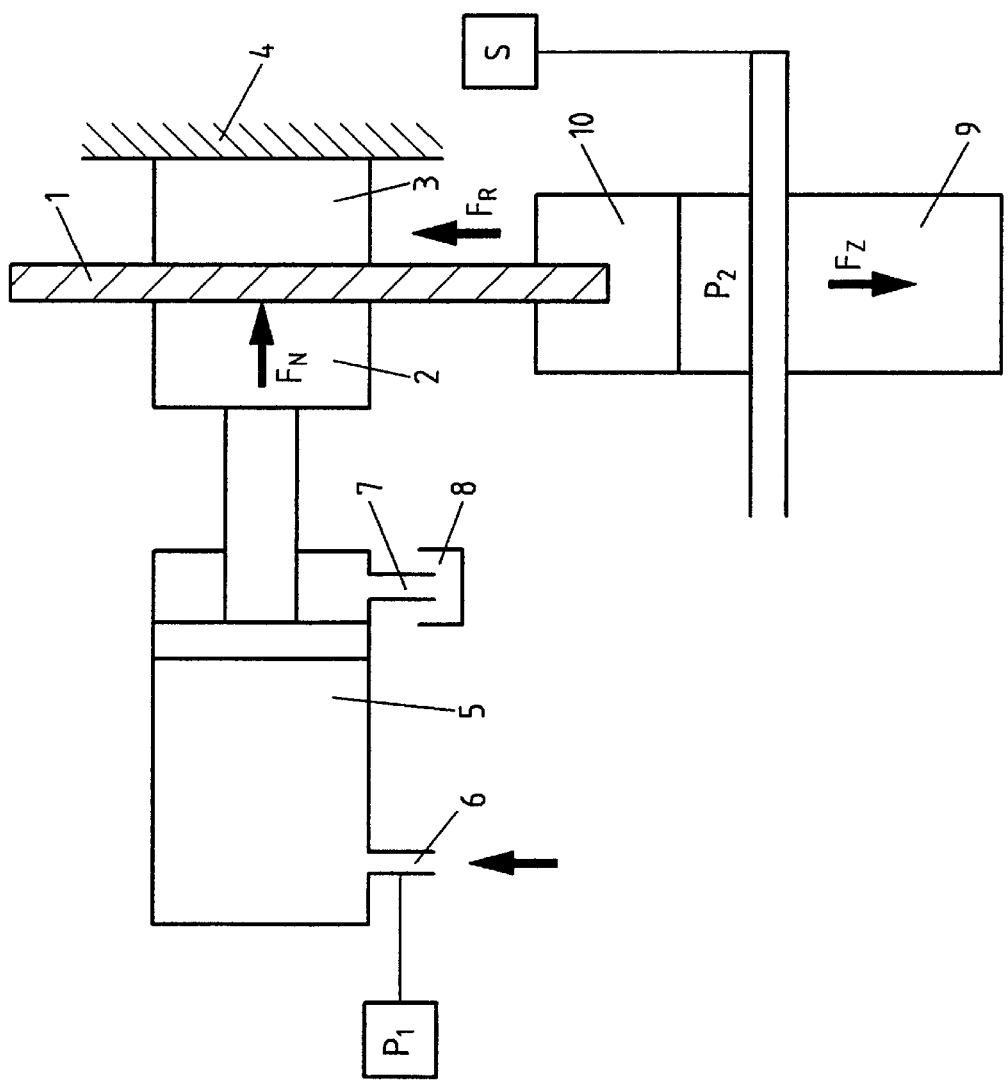

PROCESS FOR THE DETERMINATION OF THE FRICTION PROPERTIES OF SHEET METAL DURING FORMING AND THE MEASURING APPARATUS FOR CARRYING OUT THE PROCESS

In view of the fact that the friction properties of sheet metal play a determinant part during forming, such as during deep-drawing, it is important to take account of these properties during the forming of the sheet. Because of the varying surface pressures which arise during forming, it is necessary for the friction properties to be determined as a function of different surface pressures. In practice, this has been done hitherto in such a way that different sheet samples have been drawn one after another through gripping jaws at different surface pressures in each case. From the different surface pressures and the drawing force required for the drawing, the friction property of each sample of sheet is determined. It is clear that such a process is time-consuming because of the need to clamp the samples between the jaws one after another.

The objective on which the invention is based is to develop a process for the determination of the friction properties of metal sheets during forming, with which the friction properties can be determined with a broad spectrum of surface pressures.

In addition to this, the invention is based on the objective of creating a measuring apparatus for the performance of said process.

The invention accordingly relates to a process for the determination of the friction properties of sheet metal during its forming, whereby a sample of sheet metal is drawn at a given surface pressure between gripping jaws, and the drawing force necessary for the drawing is measured. Such a process is characterised according to the invention by the fact that, when the sample is drawn at a given drawing speed, the surface pressure is controlled according to a specified characteristic curve, and the friction properties dependent on the surface pressure in each case are determined from the values for the surface pressure and the drawing force assigned to one another.

With the process according to the invention, it is possible for the friction properties of a number of sheet samples to be determined rapidly in one procedure over a broad spectrum of surface pressure. It would be conceivable for the determination also to be made of the drawing speed or its incorporation, if it is varied. By contrast with the known process, with which individual sheet samples are drawn in each case with constant surface pressure through the gripping jaws, with the process according to the invention the phases which would otherwise be conventional, of the transition from adherence friction to slide friction, can be omitted, which also has a favourable effect on the measuring time required, while not impairing the indication significance of the measurement result.

In principle it is possible for the drawing of the metal sample through the gripping jaws to be effected with a drawing speed in accordance with a specified characteristic speed curve.

The change in the surface pressure can be effected in stages, as well as continuously.

A measuring device for the performance of the process is characterised by a) A pair of gripping jaws for clamping a sample of sheet metal, b) A pressure generator for the gripping jaws, the pressure force of which is adjustable, c) A drawing device which grips the sample, with which the sample can be drawn through the gripping jaws at a specified drawing speed, d) A control device for the pressure generator and/or a drive unit for the drawing device, with which the pressure force when drawing the sheet metal sample through the clamping jaws can be varied, and e) A measurement and evaluation device, which determines the friction properties from the measurement values allocated to the surface pressure of the gripping jaws and the drawing force taking effect on the sheet sample over the drawing path, and, if appropriate, also the drawing speed.

For preference, the control device consists of a regulator for the pressure generator and, if appropriate, for the drive unit of the drawing device.

Figure 2:
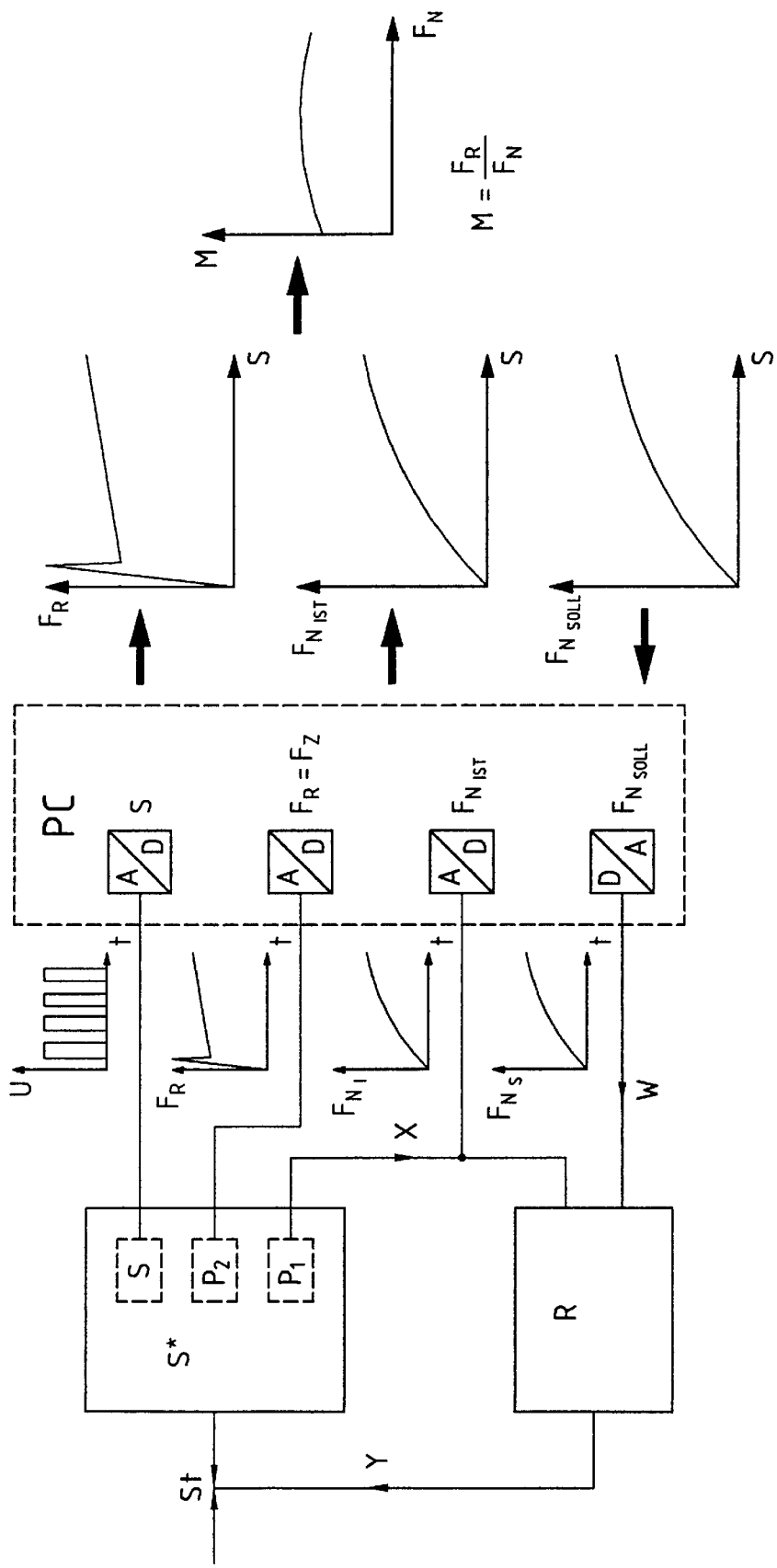

The invention is explained in greater detail hereinafter on the basis of drawings showing an embodiment of the measuring apparatus. Specifically, these show:

FIG. 1 The mechanical part of the measuring apparatus;

FIG. 2 The technical control part of the measuring apparatus and

Figure 3:
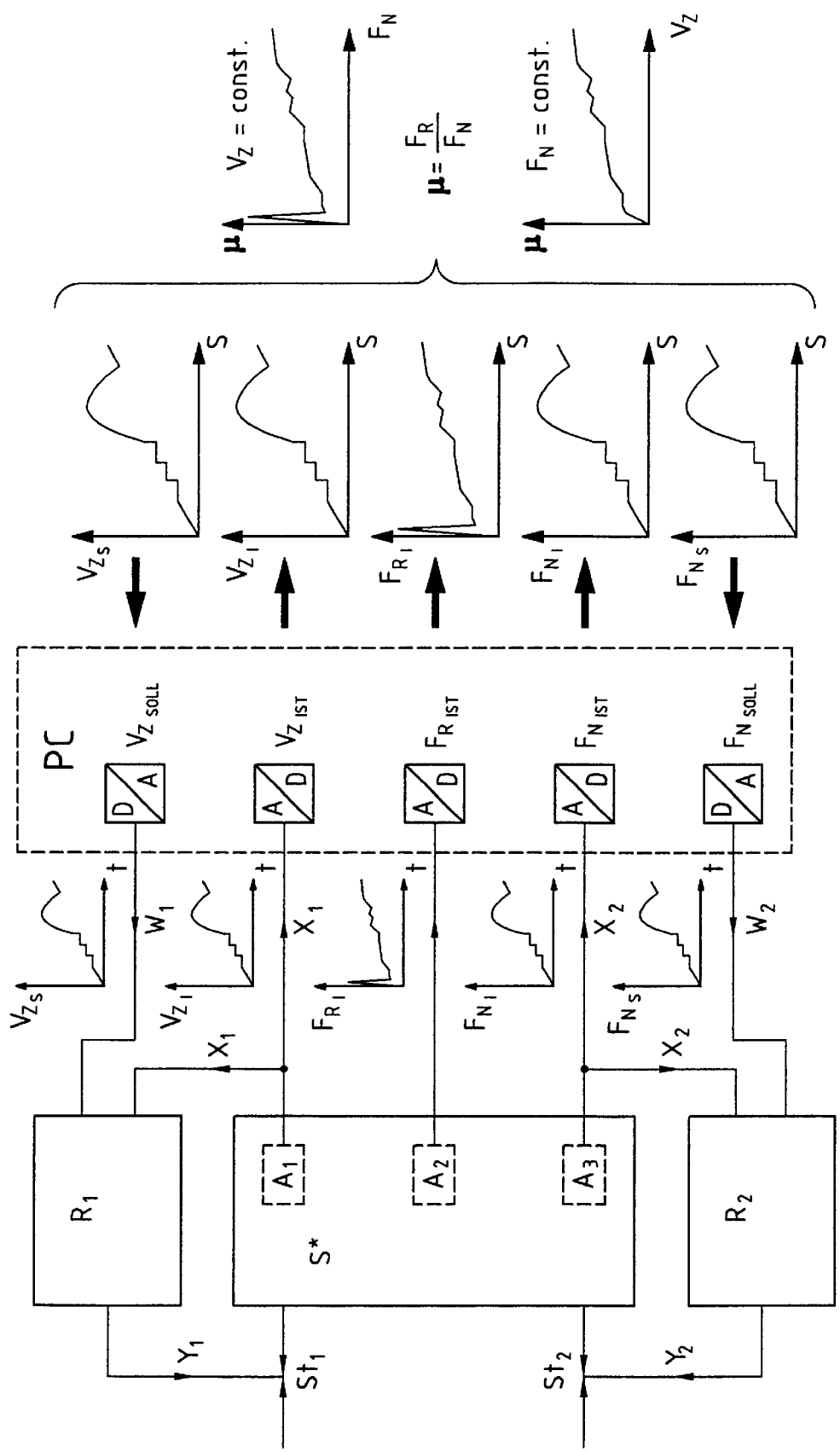

FIG. 3 A technical control part extended in relation to the technical control part of FIG. 2.

As can be seen from FIG. 1, a strip-shaped sample of sheet metal 1 is clamped between a pair of gripping jaws 2, 3. The gripping jaws 2, 3 are held in a fixed position by a holder device 4, indicated schematically. A pressure force generator 5 in the form of a hydraulic cylinder applies pressure on the gripping jaws 2 with a force $F_N$. The pressure medium is conducted via a line 6, to which a pressure sensor $P_1$ is connected. The part located opposite the part of the hydraulic cylinder 5 on which the pressure is imposed is connected via a line 7 to a tank 8 for the purpose of volume compensation.

A schematically represented drawing device 9 grips the sheet metal sample 1 by way of a clamping holder 10. Between the drawing device 9 and the clamping holder 10 is a measuring force sensor for the drawing force $F_Z$, which is equal to the holding force, $F_R$ of the gripping jaws. To determine the drawing path, a path sensor S is coupled to the drawing device 9.

The control and technical measuring part of the measuring apparatus according to FIG. 2 consists essentially of a computer PC and a regulator for the pressure force $F_N$ of the gripping jaws 2, 3 and for their surface pressure respectively. At the computer PC a time-dependent characteristic curve is specified for the reference value of the pressure force $F_{N\,SOLL}$ and therefore also for the surface pressure of the gripping jaws 2, 3. This curve is passed to the pressure sensor regulator R as a desired guide value W. The pressure sensor regulator R further receives as a regulating value from the diameter $P_1$ a measurement signal for the actual value of the pressure force $F_{N\,IST}$. The actual value of the pressure force $F_{N\,IST}$ is also passed to the computer PC. The pressure sensor regulator R develops the setting value Y from the reference and actual value for the pressure force $F_{N\,SOLL}$ and $F_{N\,IST}$, which takes effect on an actuator St, with which the pressure medium in the hydraulic cylinder 5 is to be conducted as a controlled system S* via the line 6. In addition, the computer PC receives from the path sensor S a signal for the drawing path and from the force sensor $P_2$ a signal for the drawing force $F_Z$. In the drawing the characteristic temporal curves for the reference and actual values of the pressure force and the surface pressure $F_{N\,SOLL}$, $F_{N\,IST}$ respectively, and for the drawing force $F_R=F_Z$ are shown by way of example, in each case above the signal line pertaining to them, for a constant drawing speed. These time-dependent temporal curves correspond to the drawing path dependent characteristic curves, which are shown in the drawing to the right of the computer PC.

From the measurement values for the drawing force $F_R = F_Z$ and the pressure force $F_{N\ IST}$ or the surface pressure $F_{N\ SOLL}$ respectively, the friction properties of the sheet metal sample can be calculated with the formula $\mu = F_R/F_N$ over a broad spectrum of surface pressure. This characteristic curve is shown on the right outside edge.

The technical control part of the measuring apparatus according to FIG. 3 differs from that in FIG. 2 in that, in this case, in addition to the pressure force $F_N$ via the regulator $R_1$, the drawing speed $V_Z$ is also incorporated via the regulator $R_2$. The diagram also shows that the characteristic curves for the speed $V_Z$ and for the surface pressure $F_N$ do not run constantly and continuously but in accordance with a specified and optionally selected characteristic curve.

In view of the fact that tribological differences may pertain between the two sides of a sheet, a sample can be tested to determine these properties of a side of a sheet, said sample consisting of two cut sections of sheet of the same nature. The sides of the sheet of the same nature which are to be measured are then turned towards the gripping jaws, while the two other sheet sides which are of the same nature but are not to be measured are laid on top of one another.

What is claimed is:

1. A process for determining frictional properties of a sheet metal during forming, wherein a sample of said sheet metal is drawn between gripping jaws at a specified surface pressure, comprising:

applying a specified surface pressure to said sample of sheet metal, wherein said specified surface pressure is defined according to a time-dependent predetermined characteristic curve and wherein said specified surface pressure changes continuously;

drawing said sample of sheet metal between said gripping jaws, wherein said sample of sheet metal is drawn at a drawing speed specified by a time-dependent predetermined characteristic curve;

measuring a drawing force over time, said drawing force being required to draw said sample of sheet metal between said gripping jaws at the drawing speed specified by the time-dependent predetermined characteristic curve; and calculating said frictional properties as a function of surface pressure from said specified surface pressure and from said measured drawing force.

2. The process according to claim 1, wherein the drawing speed is constant over time.

3. The process according to claim 1, wherein the drawing speed is variable over time.

4. The process according to claim 1, wherein the specified surface pressure changes in stages.

5. An apparatus to measure frictional properties of a sheet metal during forming comprising:

a) a pair of gripping jaws for clamping a sample of sheet metal;

b) a pressure generator for the gripping jaws, wherein the gripping jaws exercise an adjustable surface pressure;

c) a drawing device, which draws the sample of sheet metal through the gripping jaws at a drawing speed specified by a time-dependent predetermined characteristic curve;

d) a control device for the pressure generator and for the drawing device, wherein the control device varies at least one of the adjustable surface pressure exerted by the gripping jaws and the drawing speed when the sample of sheet metal is drawn through the gripping jaws; and e) a measurement and evaluation device for determining the frictional properties from the adjustable surface pressure of the gripping jaws and from a drawing force applied to the sample of sheet metal.

6. An apparatus according to claim 5, wherein the control device controls the pressure generator.

7. An apparatus according to claim 6, wherein the control device varies the adjustable surface pressure.

8. An apparatus according to claim 5, wherein the control device controls the drawing device.

9. An apparatus according to claim 7, wherein the control device varies the drawing speed.

10. An apparatus according to claim 5 wherein the measurement and evaluation device determines the frictional properties from the drawing speed.

11. The measuring apparatus of claim 5, wherein the control device comprises a regulator device for the pressure generator.

12. The measuring apparatus of claim 5, wherein the control device comprises a regulator device for the drawing device.

* * * * *